US012734153B2

(12) United States Patent
Yi et al.

(10) Patent No.: US 12,734,153 B2
(45) Date of Patent: Sep. 15, 2026

(54) METHODS FOR AMELIORATING AND PREVENTING AGE-RELATED MUSCLE DEGENERATION

(71) Applicant: NANJING NUTRABUILDING BIO-TECH CO., LTD., Nanjing (CN)

(72) Inventors: Ronghua Yi, Nanjing (CN); Mingru Wang, Nanjing (CN); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 402 days.

(21) Appl. No.: 18/514,875

(22) Filed: Nov. 20, 2023

(65) Prior Publication Data

US 2024/0082219 A1 Mar. 14, 2024

Related U.S. Application Data

(63) Continuation of application No. PCT/CN2022/093784, filed on May 19, 2022.

(30) Foreign Application Priority Data

May 20, 2021 (WO) ................ PCT/CN2021/094813

(51) Int. Cl.

| | |
|---|---|
| ***A61K 31/4172*** | (2006.01) |
| ***A61P 21/00*** | (2006.01) |
| ***A61P 39/06*** | (2006.01) |

(52) U.S. Cl.

CPC .......... *A61K 31/4172* (2013.01); *A61P 21/00* (2018.01); *A61P 39/06* (2018.01)

(58) Field of Classification Search

CPC .................................................. A61K 31/4172

USPC .......................................................... 514/398

See application file for complete search history.

(56) References Cited

U.S. PATENT DOCUMENTS

| | | | | |
|---|---|---|---|---|
| 6,103,746 | A * | 8/2000 | Yarosh | A61K 9/1272 424/9.1 |
| 2012/0141611 | A1 | 6/2012 | Landes et al. | |
| 2015/0157648 | A1 | 6/2015 | Hausman | |
| 2020/0222351 | A1 | 7/2020 | Dhamane et al. | |
| 2021/0130787 | A1 | 5/2021 | Kosaka | |
| 2024/0115532 | A1* | 4/2024 | Yi | A61K 31/4172 |

OTHER PUBLICATIONS

World Intellectual Property Organization (WIPO) International Search Report for PCT/CN2022/093784 Aug. 17, 2022 6 pages.

Kameda Masahiro et al., "Frailty markers comprise blood metabolites involved in antioxidation cognition and mobility", Proceedings of the National Academy of Sciences of the United States of America ,vol. 117, No. 17, Apr. 28, 2020 (Apr. 28, 2020), ISSN:0027-8424 pp. 9483-9489.

Marone Palma Ann.et al., "A safety evaluation of a nature-identical L-ergothioneine in sprague dawley rats", International Journal of Toxicology ,vol. 35, No. 5, Jun. 19, 2016 (Jun. 19, 2016), ISSN:1091-5818 pp. 568-583.

* cited by examiner

*Primary Examiner* — Niloofar Rahmani

(74) *Attorney, Agent, or Firm* — Cooper Legal Group, LLC

(57) ABSTRACT

Among others, the present invention provides methods for ameliorating and preventing age-associated muscle degeneration in a mammal, comprising administrating to the mammal in need thereof a therapeutically effective amount of L-Ergothioneine, an analog or derivative thereof, or a pharmaceutically acceptable salt, acid, ester, analog or derivative thereof, as an active ingredient. In particular, the administration of L-Ergothioneine is capable of attenuating the loss of muscle mass and/or strength in the mammal, and is capable of improving adenosine triphosphate (ATP) production, improving the P/O ratio (ATP produced per $O_2$ consumed), and/or scavenging and blocking chronic reactive oxygen species (ROS) in the mammal.

14 Claims, 5 Drawing Sheets

D

Gastrocnemius Muscle(g)

0.4
0.3
0.2
0.1
0.0

**
**

YM
OM
OM+5mg/kg/day EGT
OM+15mg/kg/day EGT
OM+45mg/kg/day EGT

METHODS FOR AMELIORATING AND PREVENTING AGE-RELATED MUSCLE DEGENERATION

CROSS-REFERENCE TO RELATED APPLICATION

This application is a continuation application of international patent Application No. PCT/CN2022/093784, filed on May 19, 2022, which claims the priority of the international application PCT/CN2021/094813, filed on May 20, 2021, the contents of which are incorporated herein by reference in their entirety.

FIELD OF THE DISCLOSURE

The present disclosure generally relates to the field of health food and dietary supplements and, more particularly, relates to methods for ameliorating and preventing age-related muscle degeneration.

BACKGROUND

Seniors tend to suffer from undernutrition, which may result from malabsorption, low protein and energy intake. Moreover, physically inactive seniors are inclined to implicate increased sedentarism, bed rest and lessen physical activity, etc. These phenomena will increase the likelihood of developing age-associated muscle degeneration. Further, recent researches have reported that muscle mass decreases by approximately 8% per decade after the age of 40 years, which rate is further increased to 15% per decade after the age of 70 years. As such, age-related muscle degeneration occurs in all individuals, especially for people aged over 60 years.

Age-related muscle degeneration can cause various disadvantages. For example, it may accelerate the loss of muscle mass/strength or weight, reduce in mobility (both in speed and dexterity), impair physical function, diminish the quality of life, and increase the risk of death. Due to these problems, age-related muscle degeneration is associated with increased adverse outcomes including prevalence of falls, fractures, functional decline, frailty, disability, hospitalization, care home admission and mortality. Therefore, along with the increasing trend of aging population, age-related muscle degeneration has been recognized as a crucial health concern in the aging society.

Moreover, age-related muscle degeneration is characterized by the contribution of mitochondrial dysfunction in the older adults, resulting in reducing protein synthesis, DNA damage, mitochondrial DNA (mtDNA) deletion-mutations.

By far, there have been some non-pharmacological methods approved for improvement and prevention of age-related muscle degeneration. While some literatures reported the pharmacological intervention to identify that the testosterone and growth hormones to help people maintain muscle mass as they age, such method not only has little effect on improving muscle mass and strength in seniors, but also may cause many side effects, such as stomachache, headache and arthralgia. See, e.g., De Spiegeleer, A., et al., *Pharmacological Interventions to Improve Muscle Mass, Muscle Strength and Physical Performance in Older People: An Umbrella Review of Systematic Reviews and Meta-analyses. Drugs Aging,* 2018. 35(8): p. 719-734; and Snyder, P. J., et al., Lessons From the Testosterone Trials. *Endocr Rev,* 2018. 39(3): p. 369-386. Also, while aerobic exercise can generally increase muscle mass/strength and improve muscle protein, seniors usually have limited ability to do exercises, let alone the aerobic exercise. Therefore, existing pharmacological and nutritional methods of reducing age-related muscle degeneration mainly aim at increasing muscle mass directly and the effects of these described approaches are not satisfactory at present. Accordingly, there remains a significant and urgent need for a strategy for alleviating and preventing the loss of muscle mass and strength in the aging subjects. Particularly, there is an urgent need for using an effective substance to fundamentally ameliorate and prevent age-associated muscle degeneration.

L-Ergothioneine is a water-soluble amino acid found mainly in mushrooms, but also in king crab, meat from animals that have grazed on grasses containing L-Ergothioneine, and other foods. L-Ergothioneine cannot be synthesized by the human body (or other vertebrates), as it can only be supplemented by diet. This compound has a wide tissue distribution in human, with a more abundant accumulation in erythrocytes, liver, seminal fluid, bone marrow, eye lens, cornea, and kidney. L-Ergothioneine is a powerful energy-boosting antioxidant. It is a naturally occurring thiol/thione derivative of the essential amino acid histidine, its molecular formula is $C_9H_{15}N_3O_2S$—combined with hydrogen, that sulfur at the end is what actually classifies it as a "thiol", the "—SH group", is either referred to as a thiol group or a sulfanyl group. Thiols have a strong affinity towards soft metals, which contributes to L-Ergothioneine's scavenging effects.

In summary, to overcome the drawbacks of conventional methods of reducing age-related muscle degeneration, it is therefore desired to have novel methods and use to effectively ameliorate and prevent age-associated muscle degeneration.

SUMMARY

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

The present invention generally relates to methods and use with administration of L-Ergothioneine as the active ingredient for ameliorating and preventing age-associated muscle degeneration in a mammal (e.g., animals or humans). According to this invention, it was surprisingly found that L-Ergothioneine can mitigate and prevent the age-related muscle degeneration radically and effectively in the ageing society, such as improving ATP production, scavenging and blocking chronic ROS. It is believed that this invention is the first time to propose and conduct L-Ergothioneine as an active ingredient to ameliorate and prevent age-related muscle degeneration.

One aspect of this invention relates to a method for ameliorating and preventing age-associated muscle degeneration in a mammal, comprising administrating to the mammal in need thereof a therapeutically effective amount of L-Ergothioneine, an analog or derivative thereof, or a pharmaceutically acceptable salt, acid, ester, analog or derivative thereof, as an active ingredient.

In some embodiments, the mammal is an old mammal. In some embodiments, the mammal is a human being. In some further embodiments, the human is aged 30 years or older (e.g., 40 years, 60 years, or 70 years).

In some embodiments, the administration of L-Ergothioneine is capable of attenuating the loss of muscle mass and/or strength in the mammal.

In some embodiments, the administration of L-Ergothioneine is capable of improving adenosine triphosphate (ATP) production, improving the P/O ratio (ATP produced per $O_2$ consumed), and/or scavenging and blocking chronic reactive oxygen species (ROS) in the mammal. Examples of ROS may include but are not limited to H2O2, hydroxyl radical and superoxide anion.

In some embodiments, L-Ergothioneine is prepared in a form of nutritional, drinking, or pharmaceutical composition, for use in food, drink, nutritional or pharmaceutical products.

In some embodiments, L-Ergothioneine is administrated as a dietary supplement or an ingredient in a food.

In some embodiments, L-Ergothioneine is administrated in a form of solutions, liquid suspensions, parenteral solutions, injections, tablets, pills, granules, powder, film, (micro)capsules, aerosols, tonics, syrups, beverages, or nourishments.

In some embodiments, L-Ergothioneine is administrated orally, by intravenous injection, by intramuscular injection, intraperitoneally or sublingually.

In some further embodiments, L-Ergothioneine is administrated by oral with a daily dose ranging from 2 mg to 2000 mg. The daily dose may be administrated by a single dose or multiple divided doses.

In some embodiments, L-Ergothioneine is administrated at least once or multiple times a day. In some further embodiments, L-Ergothioneine is administrated daily for at least seven days in one period.

Another aspect of the present invention provides a use of L-Ergothioneine for preparing a composition for effectively ameliorating and preventing age-associated muscle degeneration in a mammal, wherein the composition comprises a therapeutically effective amount of L-Ergothioneine, an analog or derivative thereof, or a pharmaceutically acceptable salt, acid, ester, analog or derivative thereof, as an active ingredient.

In some embodiments, L-Ergothioneine is prepared in a form of solutions, liquid suspensions, parenteral solutions, injections, tablets, pills, granules, powder, film, (micro) capsules, aerosols, tonics, syrups, beverages, or nourishments.

In some embodiments, L-Ergothioneine is capable of attenuating the loss of muscle mass and/or strength in the mammal.

In some embodiments, L-Ergothioneine is capable of improving adenosine triphosphate (ATP) production, improving the P/O ratio (ATP produced per $O_2$ consumed), and/or scavenging and blocking chronic reactive oxygen species (ROS) in the mammal.

Still in some embodiments, the composition comprises L-Ergothioneine with a dose ranging from 2 to 2000 mg.

As used herein, the term "or" is meant to include both "and" and "or." In other words, the term "or" may also be replaced with "and/or."

As used herein, the term "therapeutically effective amount," which can be interchanged with "physiologically effective amount," means an amount that is required to provide or result in effect in therapy or physiological conditioning, or an amount sufficient to provide a therapeutic or physiological effect. An amount that is effective in therapy or physiological conditioning is an amount which produces a biological activity (or physiological response) and will depend, among other things, on the individual.

As used herein, the term "pharmaceutically acceptable," which can be interchanged with "physiologically acceptable," means that which is useful in preparing a pharmaceutical or physiological composition (e.g., a supplement) is generally safe, non-toxic and neither biologically nor otherwise undesirable and includes that which is acceptable for veterinary uses or human pharmaceutical use.

Unless otherwise specifically indicated, the technical and scientific terms used in the framework of the present invention have generally accepted meanings known to those skilled in the art to which the invention relates. In the text of the description and claims, the singular also includes plural references, unless the context clearly dictates otherwise. As used herein, the singular forms "a," "an" and "the" are intended to include the plural forms as well, unless the context clearly indicates otherwise.

BRIEF DESCRIPTIONS OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 1A-1D show test results related to effect of EGT treatment on age-induced muscle loss in mice monthly. More specifically, FIG. 1A shows tests results regarding body weight measurement. FIG. 1B shows tests results regarding lean mass ratio. FIG. 1C shows test results regarding tissue weights of soleus muscle. FIG. 1D shows test results regarding tissue weights of gastrocnemius muscle.

Figures 4A, 4B, 4C:
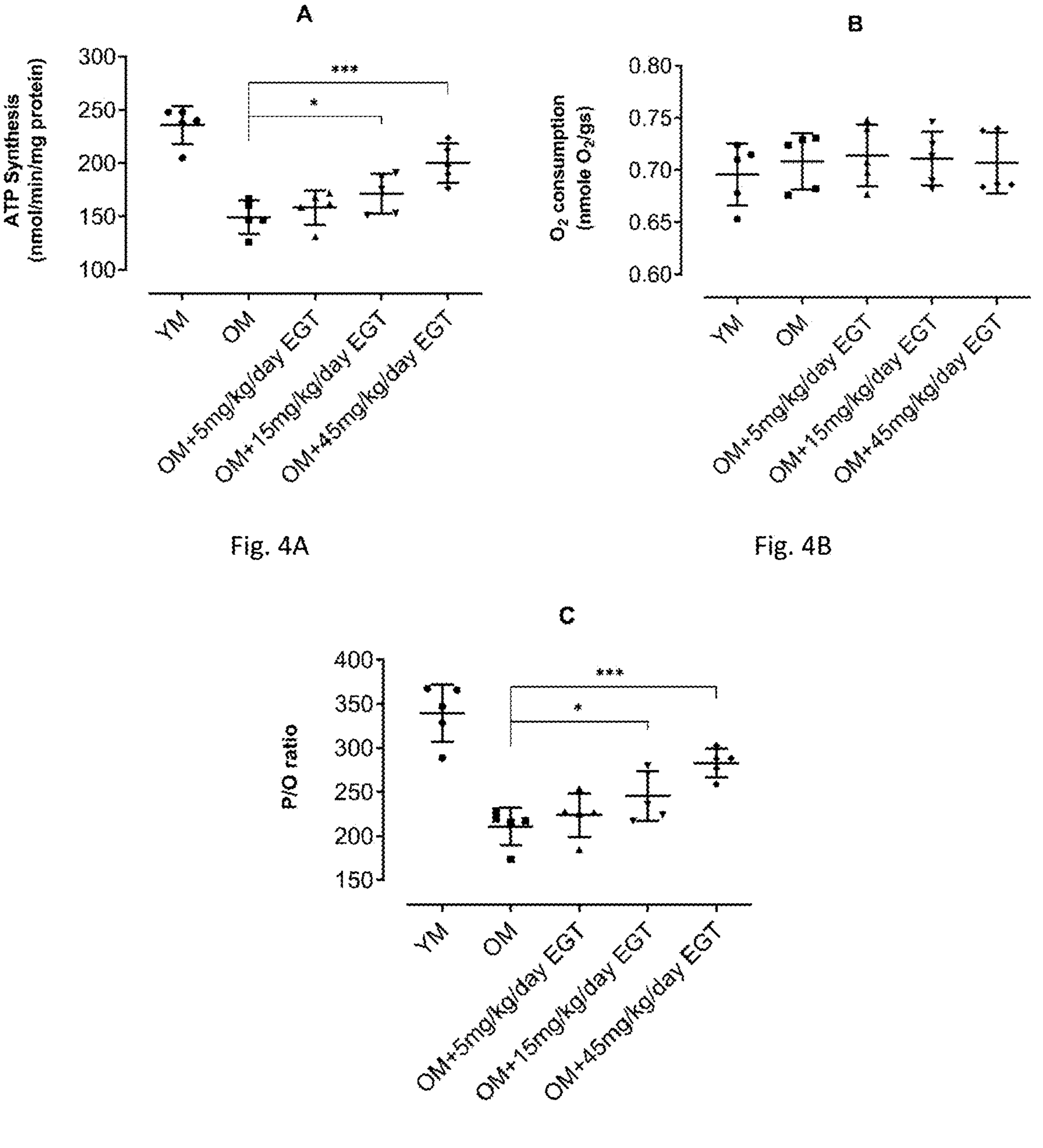

FIGS. 4A-4C show test results related to effect of EGT treatment. More specifically, FIG. 4A shows test results regarding ATP production. FIG. 4B shows test results regarding $O_2$ consumption.

FIG. 4C shoes test results regarding P/O ratio.

Figure 5A:
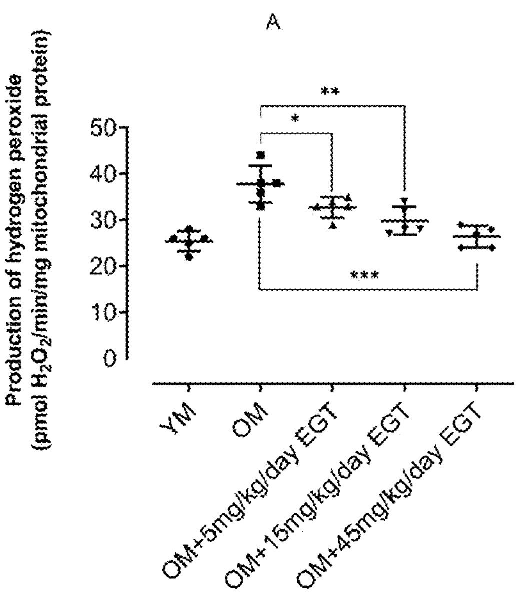
Figure 5B:
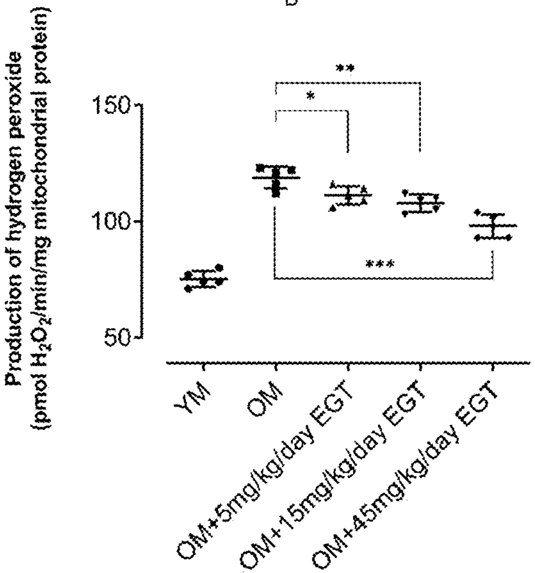

FIGS. 5A-5B show test results related to effect of EGT treatment on skeletal muscles mitochondria ROS in mice. More specifically, FIG. 5A illustrates mitochondrial hydrogen peroxide production in isolated mitochondria in State 1 (no added substrate); and FIG. 5B illustrates hydrogen peroxide production measured in mitochondria incubated with 5 mM glutamate/malate.

DETAILED DESCRIPTION

Reference will now be made in detail to the preferred embodiments of the invention, examples of which are further illustrated. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and other features have not been described in detail as not to unnecessarily obscure aspects of the present invention.

Generally speaking, various embodiments of the present invention provide for methods for administrating L-Ergothioneine (or an analog or derivative thereof, or a pharmaceutically acceptable salt, acid, ester, analog or derivative thereof) as the active ingredient to a mammal (e.g., a senior) for ameliorating and preventing age-associated muscle degeneration in a mammal. Particularly, L-Ergothioneine is able to improve adenosine triphosphate (ATP) production, improving the P/O ratio (ATP produced per O2 consumed), and/or scavenge and block chronic reactive oxygen species (ROS), and then attenuate the loss of muscle mass in the mammal. ROS may include $H_2O_2$, hydroxyl radical and superoxide anion. Moreover, L-Ergothioneine may be administrated in a variety of forms, such as solutions, liquid suspensions, parenteral solutions, injections, tablets, pills, granules, powder, film, (micro)capsules, aerosols, tonics, syrups, beverages, and nourishments. For instance, L-Ergothioneine may be administrated (e.g., by oral) with a daily dose ranging from 2 to 2000 mg for at least seven days in one period. Further, the present invention also provides use of L-Ergothioneine for preparing a composition for effectively ameliorating and preventing age-associated muscle degeneration in a mammal, wherein the composition comprises a therapeutically effective amount of L-Ergothioneine, an analog or derivative thereof, or a pharmaceutically acceptable salt, acid, ester, analog or derivative thereof, as an active ingredient.

The following examples are illustrative of select embodiments of the present invention and are not meant to limit the scope of the invention.

Examples

The healthy and male C57BL/6J mice at 20 months of age (Old Mice, OM) and at 2 months of age (Young Mice, YM) were maintained under the barrier conditions in a temperature-controlled environment and fed a commercial mouse chow. They were divided into the following five groups: (1) non-supplement young mice group (YM, n=5); (2) non-supplement old mice group (OM, n=5); (3)L-Ergothioneine supplement group with low dosage (OM+5 mg/kg/day, n=5); (4) L-Ergothioneine supplement group with moderate dosage (OM+15 mg/kg/day, n=5); and(5) L-Ergothioneine supplement group with high dosage (OM+45 mg/kg/day, n=5). All mice were administered L-Ergothioneine for once daily by gavage in normal saline solution for 4 months. Mice were euthanized by $CO_2$ inhalation followed by cervical dislocation at the end of study and skeletal muscles were excised for an immediate isolation of mitochondria.

Test 1. Mitigating the Loss of Old Mice's Muscle Mass.

The bodyweight of C57BL/6 mice was recorded before treatment, once per week during the study, and at the end of the study. Body composition (lean mass ratio) of mice was analyzed using the (NM42-040H-1 system, Suzhou Niumag) before treatment, once per month during the study, and at the end of the study.

Figure 1A:
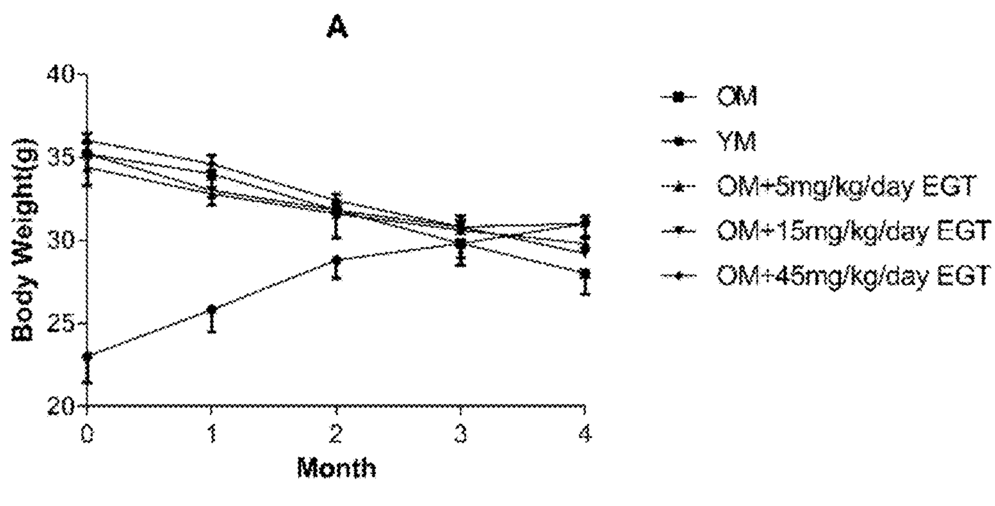
Figure 1B:
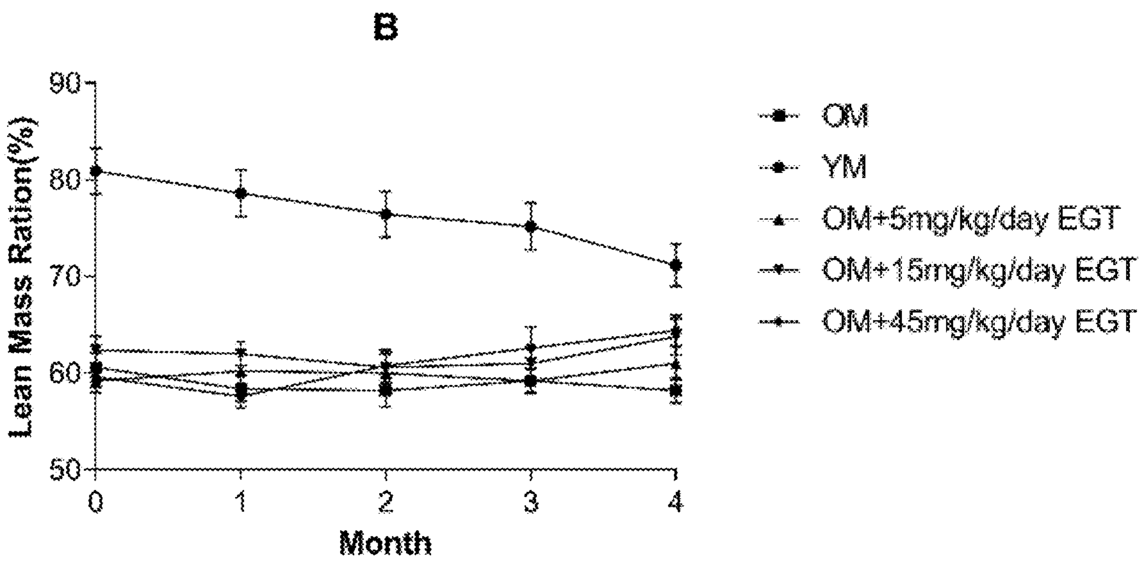
Figures 1C, 1D:
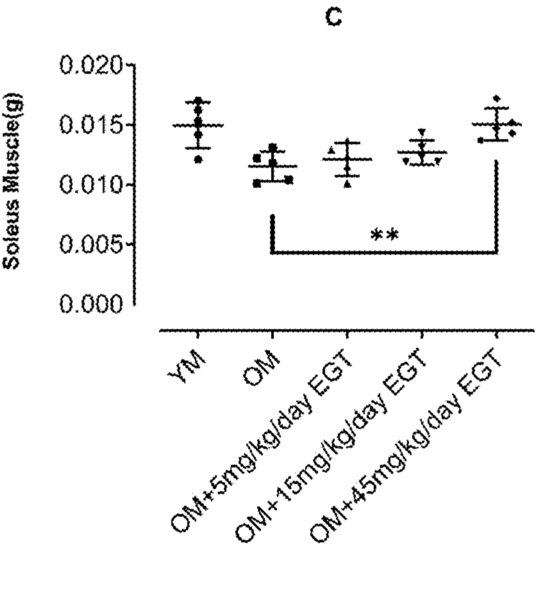

FIGS. 1A-1D show the test results related to effect of EGT treatment on age-induced muscle loss in mice monthly, particularly regarding body weight measurement (FIG. 1A), lean mass ratio (FIG. 1B), tissue weights of soleus muscle (FIG. 1C), and tissue weights of gastrocnemius muscle (FIG. 1D). Statistical significance was determined using one-way ANOVA followed by Tukey's post hoc test (N=5, *P<0.05, **P<0.01, vs OM Group).

As shown in FIGS. 1A-1D, there were no significant difference in body weight (FIG. 1A) and body composition (lean mass ratio) (FIG. 1B) between OM and administration Groups. However, the weight of the soleus muscle and the gastrocnemius muscle in OM Group was markedly reduced, suggesting that the muscle mass was decreased due to natural aging. Ergothioneine prevented this reduction after 4 months administration (see FIGS. 1C-1D).

Test 2. Relieves the Loss of Muscle Grip Strength.

Forelimb grip strength were analyzed using the rip strength meter (Bioseb, BIO-GS3) with mouse-specific wire grid (100×80 mm, angled 90° (vertical)), once per month during the study and at the end of the study.

Figure 2:
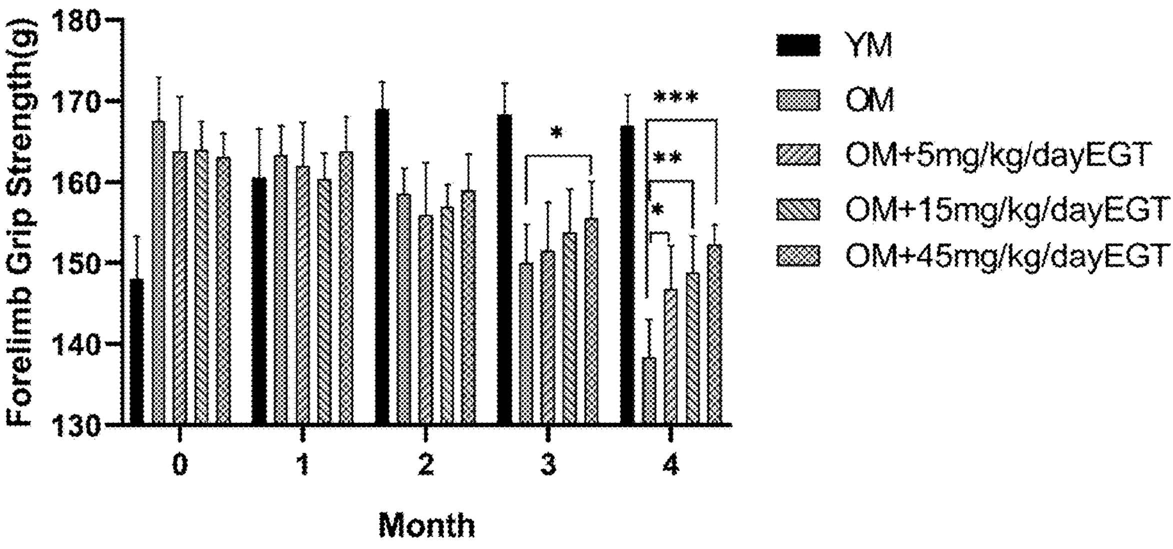
FIG. 2 shows test results related effect of EGT treatment on forelimb grip strength in mice.

FIG. 2 shows the test results related to effect of EGT treatment on forelimb grip strength in mice. Statistical significance was determined using one-way ANOVA followed by Tukey's post hoc test (N=5, *P<0.05, P<0.01, *P<0.001 vs OM Group).

As shown in FIG. 2, 57BL/6J mice demonstrated age-related impairments in strength. The changes of forelimb grip strength in Ergothioneine proved the L-Ergothioneine effects for ameliorating and preventing the loss of muscle grip strength induced by ageing.

Test 3. Ameliorate Motor Coordination Deficits.

Motor coordination deficits were performed by placing the mouse on a rotating rod (Beijing Zhishuduobao, DB093) and measuring how long it takes before mice fall off the rod (Time to Fall (s)).

Figure 3:
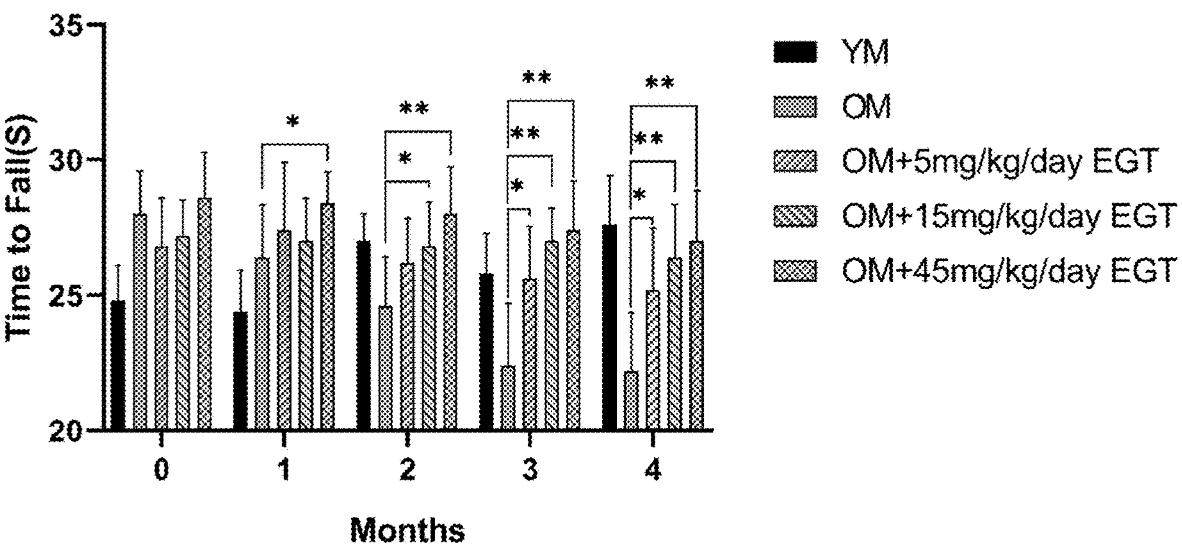
FIG. 3 shows test results related to effect of EGT treatment on motor coordination deficits in mice.

FIG. 3 shows test results related to the effect of EGT treatment on motor coordination deficits in mice. Statistical significance was determined using one-way ANOVA followed by Tukey's post hoc test (N=5, *P<0.05, **P<0.01, vs OM Group).

As shown in FIG. 3, 57BL/6J mice demonstrated age-related motor coordination deficits. The prolong time of maintain on a rotating rod proved the L-Ergothioneine effects for ameliorating and preventing the motor coordination deficits induced by ageing.

Test 4. Improving ATP Production and P/O Ratio.

Extracting skeletal muscles mitochondria from mice to measure ATP production and $O_2$ consumption. ATP production was measured using a luciferase/luciferin based system. O2 consumption was measured using optical spectra. The all data were analyzed to identify the L-Ergothioneine function for improving ATP production and $O_2$ consumption.

FIGS. 4A-4C show test results related to the effect of EGT treatment on ATP synthesis (FIG. 4A), $O_2$ consumption (FIG. 4B), and P/O ratio (FIG. 4C) in mice. Statistical significance was determined using one-way ANOVA followed by Tukey's post hoc test (N=5, *P<0.05, P<0.01, *P<0.001 vs OM Group).

As shown in FIGS. 4A-4C, 57BL/6J mice demonstrated age-related ATP production deficits. The increase of ATP synthesis and P/O ratio proved the L-Ergothioneine effects for improving ATP production and P/O ratio.

Test 5. Scavenging and Blocking Chronic ROS.

Extracting skeletal muscles mitochondria from mice to measure hydrogen peroxide ($H_2O_2$, extra-mitochondrial release of $H_2O_2$ is used as the measure of ROS production). The $H_2O_2$ was determined with Amplex™ Red-horseradish peroxidase. All the data were analyzed to identify the L-Ergothioneine function for scavenging and blocking chronic ROS.

FIGS. 5A-5B show the effect of EGT treatment on skeletal muscles mitochondria ROS in mice. Statistical significance was determined using one-way ANOVA followed by Tukey's. post hoc test (N=5, *P<0.05, P<0.01, vs OM Group). In particular, FIGS. 5A-5B show production of hydrogen peroxide by isolated skeletal muscle mitochondria-including mitochondrial hydrogen peroxide production in isolated mitochondria in State 1 (no added substrate) (see FIG. 5A); and hydrogen peroxide production measured in mitochondria incubated with 5 mM glutamate/malate (see FIG. 5**B).

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

OTHER EMBODIMENTS

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. A method for ameliorating age-associated muscle degeneration in a mammal, comprising administrating to the mammal in need thereof a therapeutically effective amount of L-Ergothioneine, an analog or derivative thereof, or a pharmaceutically acceptable salt, acid, ester, analog or derivative thereof, as an active ingredient.

2. The method of claim 1, wherein the mammal is at least 30 years of age.

3. The method of claim 1, wherein the mammal is a human.

4. The method of claim 3, wherein the human is aged 30 years or older.

5. The method of claim 1, wherein the L-Ergothioneine is administrated to attenuate at least one of loss of muscle mass or strength in the mammal.

6. The method of claim 1, wherein the L-Ergothioneine is administrated to ameliorate motor coordination deficits.

7. The method of claim 1, wherein the L-Ergothioneine is administrated to at least one of:

improve adenosine triphosphate (ATP) production and ATP produced per $O_2$ consumed (P/O) ratio, or scavenge and block chronic reactive oxygen species in the mammal.

8. The method of claim 7, wherein the chronic reactive oxygen species comprise $H_2O_2$, hydroxyl radical or superoxide anion.

9. The method of claim 1, wherein the L-Ergothioneine is prepared in a form of nutritional, drinking, or pharmaceutical composition, for use in food, drink, nutritional or pharmaceutical products.

10. The method of claim 9, wherein the L-Ergothioneine is administrated as a dietary supplement or an ingredient in a food.

11. The method of claim 1, wherein the L-Ergothioneine is administrated in a form of solutions, liquid suspensions, parenteral solutions, injections, tablets, pills, granules, powder, film, (micro) capsules, aerosols, tonics, syrups, beverages, or nourishments.

12. The method of claim 1, wherein the L-Ergothioneine is administrated orally, by intravenous injection, by intramuscular injection, intraperitoneally or sublingually.

13. The method of claim 12, wherein the L-Ergothioneine is administrated orally with a daily dose ranging from 2 mg to 2000 mg.

14. The method of claim 13, wherein the daily dose is administrated by a single dose or multiple divided doses.

* * * * *